United States Patent
Sauve et al.

(10) Patent No.: US 9,603,862 B2
(45) Date of Patent: Mar. 28, 2017

(54) ACTIVATION AND ACTIVATORS OF SIRT5

(75) Inventors: Anthony Sauve, New Rochelle, NY (US); Yana Cen, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 13/516,190

(22) PCT Filed: Dec. 14, 2010

(86) PCT No.: PCT/US2010/060334
§ 371 (c)(1),
(2), (4) Date: Jun. 14, 2012

(87) PCT Pub. No.: WO2011/081942
PCT Pub. Date: Jul. 7, 2011

(65) Prior Publication Data
US 2012/0329748 A1    Dec. 27, 2012

Related U.S. Application Data (60) Provisional application No. 61/286,259, filed on Dec. 14, 2009.

(51) Int. Cl.
| | | |
|---|---|---|
| *A61K 31/706* | (2006.01) | |
| *A61K 31/341* | (2006.01) | |
| *A61K 31/443* | (2006.01) | |
| *C07D 405/04* | (2006.01) | |
| *C07H 19/048* | (2006.01) | |

(52) U.S. Cl.
CPC .......... *A61K 31/706* (2013.01); *A61K 31/341* (2013.01); *A61K 31/443* (2013.01); *C07D 405/04* (2013.01); *C07H 19/048* (2013.01)

(58) Field of Classification Search
CPC .. A61K 31/341; A61K 31/443; A61K 31/706; A61K 2300/00; C07D 405/04; C07H 19/048
USPC .................... 514/43, 52; 536/22.1
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,837,028 A | 6/1989 | Allen |
| 5,019,369 A | 5/1991 | Presant et al. |
| 2006/0014705 A1 * | 1/2006 | Howitz et al. .......... 514/27 |
| 2008/0194803 A1 * | 8/2008 | Sinclair et al. ......... 536/23.2 |

OTHER PUBLICATIONS

Nakagawa et al. (Aging, Jun. 2009, vol. 1No. 6, pp. 578-581).*
Banker and Chalmers, eds., Pharmaceutics and Pharmacy Practice, J. B. Lippincott Company, Philadelphia, pp. 238-250 (1982).
Brunet et al., Science, 303: 2011-2015 (2004).
Guarente, Nature, 444: 868-874 (2006).
Haigis et al., Cell, 126: 941-954 (2006).
Hallows et al., Proc. Natl. Acad. Sci. USA, 103: 10230-10235 (2006).
Imai et al., Nature, 403: 795-800 (2000).
Lin et al., Nature, 418: 344-348 (2002).
Onyango et al., Proc. Natl. Acad. Sci. USA, 99: 13653-13658 (2002).
Rodgers et al., Nature, 434: 113-118 (2005).
Sauve et al., Annu. Rev. Biochem., 75: 435-436 (2006).
Schlicker et al., J. Mol. Biol., 382: 790-801 (2008).
Schuetz et al., Cell, 15: 388-389 (2007).
Schwer et al., Proc. Natl. Acad. Sci. USA, 103: 10224-10229 (2006).
Sener et al., Nature, 288: 187-189 (1980).
Szoka et al., Ann. Rev. Biophys. Bioeng., 9: 467 (1980).
Toissel, *ASHP Handbook on Injectable Drugs*, 4th ed., pp. 622-630 (1986).
Vaziri et al., Cell, 107: 149-159 (2001).
Yeung et al., EMBO J., 23: 2369-2380 (2004).

\* cited by examiner

*Primary Examiner* — Shaojia Anna Jiang
*Assistant Examiner* — Michael C Henry
(74) *Attorney, Agent, or Firm* — Leydig, Voit & Mayer, Ltd.

(57) ABSTRACT

The invention provides a method of increasing a deacetylase activity of SIRT5 by contacting SIRT5 with an agent that binds SIRT5 and reduces the $K_m$ of SIRT5 for a substrate, thereby increasing the deacetylase activity of SIRT5. The invention also provides a method for treating a urea cycle disorder in a mammal, as well as a method of assaying a sirtuin modulator.

14 Claims, 5 Drawing Sheets

ACTIVATION AND ACTIVATORS OF SIRT5

CROSS-REFERENCE TO RELATED APPLICATIONS

This patent application is the U.S. national phase of International Patent Application No. PCT/US2010/060334, filed Dec. 14, 2010, which claims the benefit of U.S. Provisional Patent Application No. 61/286,259, filed Dec. 14, 2009, each of which is incorporated by reference herein.

STATEMENT REGARDING FEDERALLY SPONSORED RESEARCH AND DEVELOPMENT

This invention was made with Government support under Grant Number R01 DK73466-05 awarded by the NIH. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,440 Byte ASCII (Text) file named "710577_ST25.txt," created on Aug. 27, 2012.

BACKGROUND OF THE INVENTION

The sirtuins are highly conserved enzymes that are found in organisms ranging from bacteria to humans. In yeast, Sir2 was studied to slow aging by silencing transcription through histone deacetylation in an $NAD^+$ dependent manner (Sauve et al., *Annu. Rev. Biochem.*, 75: 435-436 (2006); Imai et al., *Nature*, 403: 795-800 (2000)). The mammalian ortholog NAD-dependent deacetylase, SIRT1, has numerous known substrates, including PGC1-a, NF-kB, p53, and FOXO1 (Brunet et al., *Science*, 303: 2011-2015 (2004); Rodgers et al., *Nature*, 434: 113-118 (2005); Yeung et al., *EMBO J.*, 23: 2369-2380 (2004); Vaziri et al., *Cell*, 107: 149-159 (2001)). Many other $NAD^+$ dependent protein deacetylases have been identified and found to regulate a variety of cellular processes such as DNA silencing, metabolic control, apoptosis, and cell cycling regulation (Guarente, *Nature*, 444: 868-874 (2006); Lin et al., *Nature*, 418: 344-348 (2002)).

Among the seven mammalian sirtuins (SIRT1 to −7), three sirtuins (SIRT3, 4 and 5) localize to mitochondria although less is known about the substrates in mitochondrial organelles (Onyango et al., *Proc. Natl. Acad. Sci. USA*, 99: 13653-13658 (2002); Haigis et al., *Cell*, 126: 941-954 (2006)). SIRT3 is known as a $NAD^+$ dependent deacetylase involved in deacetylation of acetyl-CoA synthetase 2 and found to regulate global mitochondrial acetylation (Hallows et al., *Proc. Natl. Acad. Sci. USA*, 103: 10230-10235 (2006); Schwer et al., *Proc. Natl. Acad. Sci. USA*, 103: 10224-10229 (2006)). SIRT4 is a ADP-ribosyntransferase and regulates glutamate dehyderogenase (GDH) enzyme activity by transferring ADP-ribose to repress the activity of glutamate conversion to α-ketoglutarate (Sener et al., *Nature*, 288: 187-189 (1980)).

For SIRT5, its physiological substrates, functions, and the localization in mitochondria have been indecisive (Haigis et al., supra; Schlicker et al., *J. Mol. Biol.*, 382: 790-801 (2008)). It was reported that SIRT5 is a $NAD^+$ dependent deacetylase, localized in mitochondrial matrix (Schuetz et al., *Cell*, 15: 388-389 (2007)). Activation of SirT5 is known to deacetylate the mitochondrial enzyme carbomoyl phosphate synthetase 1 (CPS1). As mitochondria are key players in metabolism, energy maintenance, and apoptosis, disruption of mitochondrial pathways can lead to metabolic disease, oxidative damage, and cancer, and activation of those same pathways can treat or prevent metabolic disease, oxidative damage, and cancer. Activation of these pathways can also mimic caloric restriction and treatment for aging and prevention of senescence.

BRIEF SUMMARY OF THE INVENTION

The invention provides a method of increasing a deacetylase activity of SIRT5, wherein the method comprises contacting SIRT5 with an agent that binds SIRT5 and reduces the $K_m$ of SIRT5 for a substrate, thereby increasing the deacetylase activity of SIRT5.

The invention also provides a method for treating a urea cycle disorder in a mammal, which method comprises administering to a mammal in need of treatment a therapeutically effective amount of a compound of the formula (I):

wherein $R^1$ and $R^2$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^3$ and $R^4$ are independently selected from the group consisting of hydrogen, hydroxyl, sulfhydryl, amino, alkylamino, dialkylamino, and halogen, $R^5$, $R^7$, $R^8$, and $R^9$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^7$ and $R^8$ taken together, or $R^8$ and $R^9$ taken together, form a 5- or 6-membered saturated or unsaturated ring, $R^6$ is selected from the group consisting of hydrogen, $COR^{10}$, $B(OR^{11})_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{10}$ is selected from the group consisting of hydrogen, amino, alkylamino, dialkylamino, hydroxy, alkoxy, and aryloxy, and $R^{11}$ is hydrogen or $C_1$-$C_6$ alkyl, thereby treating a urea cycle disorder in the mammal.

The invention further provides a method of assaying a sirtuin modulator, which method comprises (a) initiating a reaction of a sirtuin, a peptide substrate, and a radiolabelled $NAD^+$ in the presence or absence of a test compound to provide a reaction mixture, (b) loading the reaction mixture onto a purification column, (c) eluting the purification column with an eluent to provide fractions, (d) quantifying the radioactivity of the fractions, (e) determining a turnover rate from the radioactivity of the fractions, and (f) determining whether the test compound activated, inhibited, or had no effect on sirtuin activity.

DETAILED DESCRIPTION OF THE INVENTION

The invention provides a method of increasing a deacetylase activity of SIRT5, wherein the method comprises contacting SIRT5 with an agent that binds SIRT5 and reduces the $K_m$ of SIRT5 for a substrate, thereby increasing the deacetylase activity of SIRT5.

Compounds that increase the deacetylase activity of SIRT5 are referred to herein as "activating compounds." In certain embodiments, the method may comprise contacting SIRT5 with an activating compound having a structure represented by formula (I) as described herein.

SIRT5 may be activated in vitro, e.g., in a solution or in a cell. In one embodiment, SIRT5 is contacted with an activating compound in a solution. SIRT5 is activated by a compound when at least one of its biological activities, e.g., deacetylation activity, is higher in the presence of the compound than in its absence. Activation may be by a factor of at least about 10%, 30%, 50%, 100% (i.e., a factor of two), 3, 10, 30, or 100. The extent of activation can be determined, e.g., by contacting the activated SIRT5 with a deacetylation substrate and determining the extent of deacetylation of the substrate, as further described herein. The observation of a lower level of acetylation of the substrate in the presence of a test SIRT5 relative to the presence of a non-activated control SIRT5 indicates that the test SIRT5 is activated. The solution may be a reaction mixture. The solution may be in a dish, e.g., a multiwell dish. SIRT5 may be prepared recombinantly or isolated from cells according to methods known in the art.

In another embodiment, a cell comprising SIRT5 is contacted with an activating compound. The cell may be a eukaryotic cell, e.g., a mammalian cell, such as a human cell, a yeast cell, a non-human primate cell, a bovine cell, an ovine cell, an equine cell, a porcine cell, a sheep cell, a bird (e.g., chicken or fowl) cell, a canine cell, a feline cell or a rodent (mouse or rat) cell. It can also be a non-mammalian cell, e.g., a fish cell. Yeast cells include *S. cerevesiae* and *C. albicans*. The cell may also be a prokaryotic cell, e.g., a bacterial cell. The cell may also be a single-cell microorganism, e.g., a protozoan. The cell may also be a metazoan cell, a plant cell or an insect cell. Preferably, the cell is a eukaryotic cell In one embodiment, the cells are in vitro. A cell may be contacted with a solution having a concentration of an activating compound of less than about 0.1 μM, 0.5 μM, less than about 1 μM, less than about 10 μM, less than about 100 μM, less than about 250 μM, less than about 500 μM, or less than about 1000 μM. The concentration of the activating compound may also be in the range of about 0.1 to 1 μM, about 1 to 10 μM, about 10 to 100 μM, 10 to 250 μM, 10 to 500 μM, or 10 to 1000 μM. The appropriate concentration may depend on the particular compound and the particular cell used as well as the desired effect. For example, a cell may be contacted with a "SIRT5 activating" concentration of an activating compound, e.g., a concentration sufficient for activating the SIRT5 by a factor of at least 10%, 30%, 50%, 100%, 3, 10, 30, or 100.

In certain embodiments, a cell is contacted with an activating compound in vivo, such as in a subject. The subject can be a human, a non-human primate, a bovine, an ovine, an equine, a porcine, a sheep, a canine, a feline or a rodent (mouse or rat). For example, an activating compound may be administered to a subject. Administration may be local, e.g., topical, parenteral, oral, or other depending on the desired result of the administration (as further described herein). Administration may be followed by measuring a factor in the subject or the cell, such as the activity of the SIRT5 or a clinical marker of a urea cycle disorder such as levels of ammonia, ornithine, uracil, orotic acid, citrulline, arginosuccinic acid, and/or arginine. In an illustrative embodiment, a cell is obtained from a subject following administration of an activating compound to the subject, such as by obtaining a biopsy, and the activity of the SIRT5 is determined in the biopsy. The cell may be any cell of the subject, but in cases in which an activating compound is administered locally, the cell is preferably a cell that is located in the vicinity of the site of administration.

In one embodiment, a screening assay comprises (i) contacting a SIRT5 with a test agent and an acetylated substrate under conditions appropriate for the SIRT5 to deacetylate the substrate in the absence of the test agent, and (ii) determining the level of acetylation of the substrate, wherein a lower level of acetylation of the substrate in the presence of the test agent relative to the absence of the test agent indicates that the test agent stimulates deacetylation by the SIRT5, whereas a higher level of acetylation of the substrate in the presence of the test agent relative to the absence of the test agent indicates that the test agent inhibits deacetylation by the SIRT5.

Methods for identifying an agent that modulates, e.g., stimulates or inhibits, SIRT5 in vivo may comprise (i) contacting a cell with a test agent and a substrate that is capable of entering a cell under conditions appropriate for the SIRT5 to deacetylate the substrate in the absence of the test agent, and (ii) determining the level of acetylation of the substrate, wherein a lower level of acetylation of the substrate in the presence of the test agent relative to the absence of the test agent indicates that the test agent stimulates deacetylation by SIRT5, whereas a higher level of acetylation of the substrate in the presence of the test agent relative to the absence of the test agent indicates that the test agent inhibits deacetylation by SIRT5. The method may further comprise lysing the cells to determine the level of acetylation of the substrate. Substrates may be added to cells at a concentration ranging from about 0.001 to about 1 mM, preferably from about 0.01 mM to about 1 mM, and more preferably from about 0.1 mM to about 1 mM.

The acetylated substrate can be any suitable substrate that undergoes deacetylation by the action of SIRT5. The acetylated substrate can be an endogenous substrate, for example the substrate can be carbamoyl phosphate synthetase 1 (CPS1) which participates in the urea cycle. Non-limiting examples of other suitable substrates include p300, H3, H4, JB12, cytochrome C and acetylated bovine serum albumin. The sequences of the aforesaid substrates, except for acetylated bovine serum albumin, can be as described herein.

In some embodiments, whether in vitro or in vivo, a cell may also be contacted with more than one agent. Preferably, at least one agent comprises an activating compound as described herein. Additional agent(s) may comprise at least one activating compound but can comprise at least one inhibiting compound, e.g., an agent that inhibits the deacetylase activity of SIRT5. In such embodiments, the activity of SIRT5 can be modulated by the differing actions of the activating compound and the inhibiting compound. An example of an inhibiting compound which inhibits the deacetylase activity of SIRT5 is suramin.

In certain embodiments, the method comprises contacting SIRT5 with an agent, wherein the agent is a compound of the formula (I):

(I)

wherein $R^1$ and $R^2$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^3$ and $R^4$ are independently selected from the group consisting of hydrogen, hydroxyl, sulfhydryl, amino, alkylamino, dialkylamino, and halogen, $R^5$, $R^7$, $R^8$, and $R^9$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^7$ and $R^8$ taken together, or $R^8$ and $R^9$ taken together, form a 5- or 6-membered saturated or unsaturated ring, $R^6$ is selected from the group consisting of hydrogen, $COR^{10}$, $B(OR^{11})_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{10}$ is selected from the group consisting of hydrogen, amino, alkylamino, dialkylamino, hydroxy, alkoxy, and aryloxy, and

$R^{11}$ is hydrogen or $C_1$-$C_6$ alkyl, thereby increasing SIRT5 activity in the subject.

In certain embodiments, $R^3$ and $R^4$ are independently selected from the group consisting of hydrogen, hydroxyl, and halogen.

In certain embodiments, $R^1$ is hydrogen or phosphate.
In certain embodiments, $R^2$ is hydrogen.
In certain embodiments, $R^5$, $R^7$, $R^8$, and $R^9$ are hydrogen.
In certain embodiments, $R^6$ is $COR^{10}$.
In preferred embodiments, $R^{10}$ is amino.
In certain embodiments, $R^3$ is hydrogen and $R^4$ is hydroxyl.
In preferred embodiments, $R^3$ and $R^4$ are both fluoro.
In preferred embodiments, $R^3$ is hydrogen and $R^4$ is chloro.
In certain embodiments, $R^6$ is $B(OR^{11})_2$.

Figure 1:
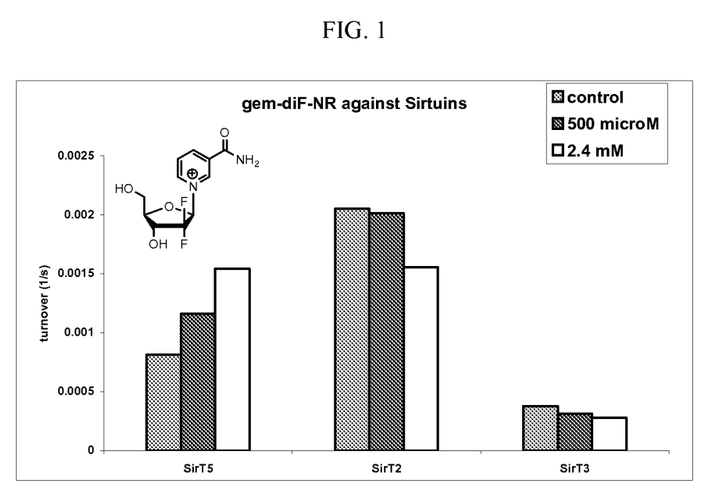
FIG. 1 demonstrates the effects of gem-difluoronicotinamide riboside on sirtuin activity.
Figure 2:
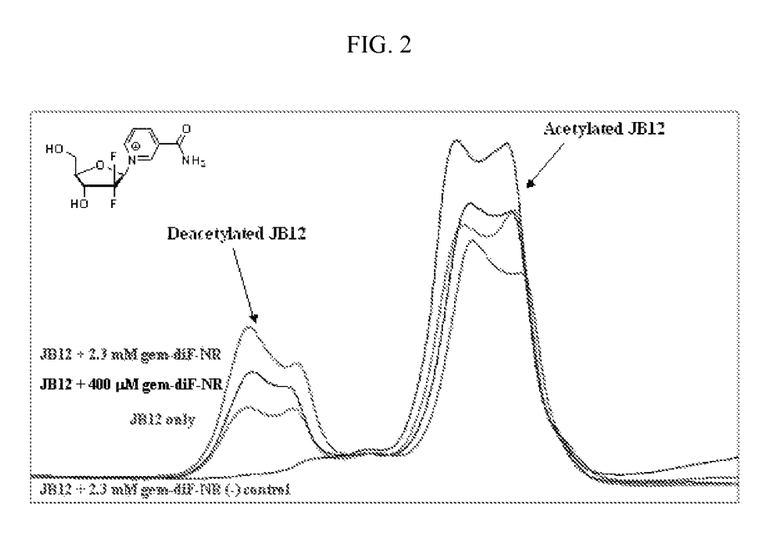
FIG. 2 depicts HPLC chromatogram overlays of gem-difluoronicotinamide riboside activated SirT5 deacetylation.
Figure 3:
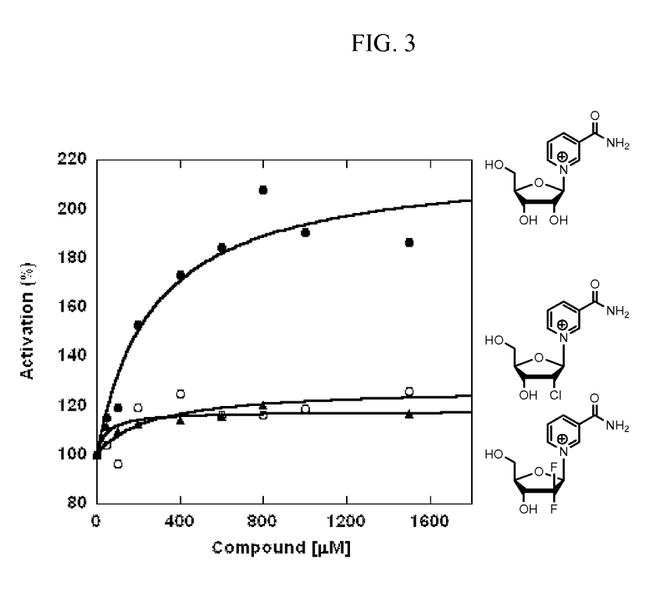
FIG. 3 depicts nicotinamide riboside (NR), ribo-Cl-NR and gem-diF-NR activation of deacetylation catalyzed by SIRT5. Top curve (solid circles): varying concentrations of nicotinamide riboside, 500 μM $NAD^+$, and 500 μM JB12, middle curve (open circles): varying concentrations of Ribo-Cl-NR, 500 μM $NAD^+$, and 500 μM JB12, bottom curve (triangles): varying concentrations of gem-diF-NR, 500 μM $NAD^+$, and 500 μM JB12. The reactions were processed using DEAE columns. The Km values of 271 μM (200% max), 95 μM (125% max), and 50 μM (120% max) were obtained from Michaelis Menten curve fitting with Kaleida-Graph for NR, ribo-Cl-NR, and gem-diF-NR, respectively.
Figure 4:
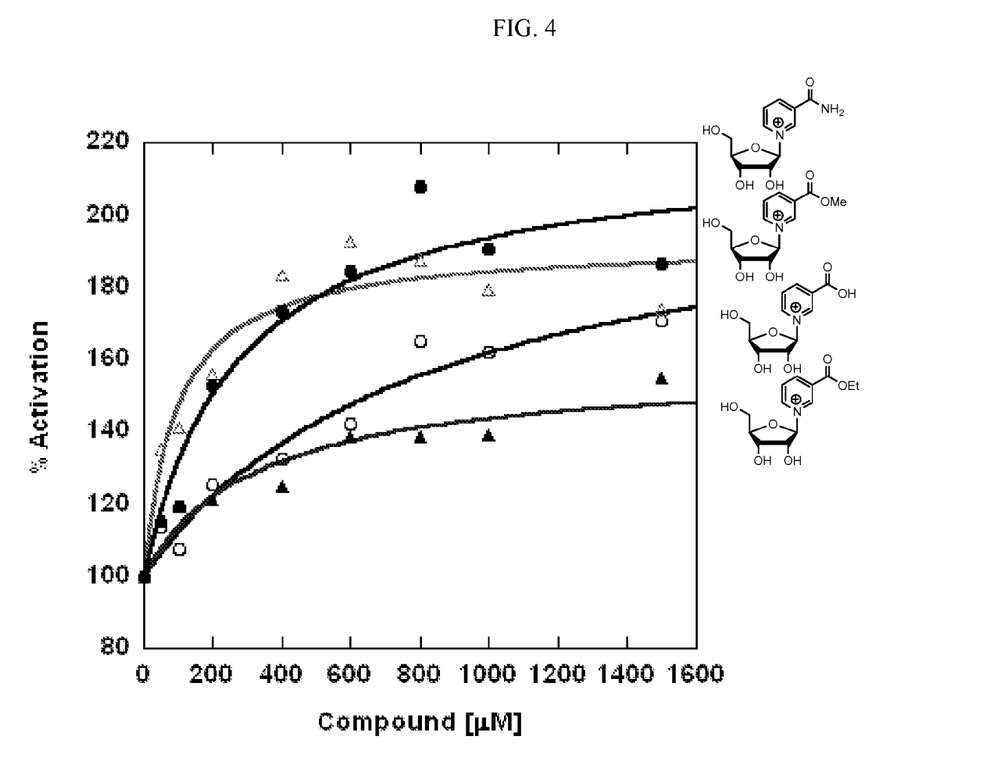
FIG. 4 demonstrates that nicotinamide riboside (NR) and its derivatives activate SIRT5 catalyzed deacetylation. Reactions contain 500 μM JB12, 500 μM $NAD^+$, and 1 mM of activator compound. Solid circles: NR (Km of 270 μM max 200%), open circles: NaR (Km of 821 μM, max 160%), solid triangles: O-ethyl NR (Km of 323 μM, max 150%), open triangles: O-methyl NR (Km of 93 μM, max 190%).
Figure 5:
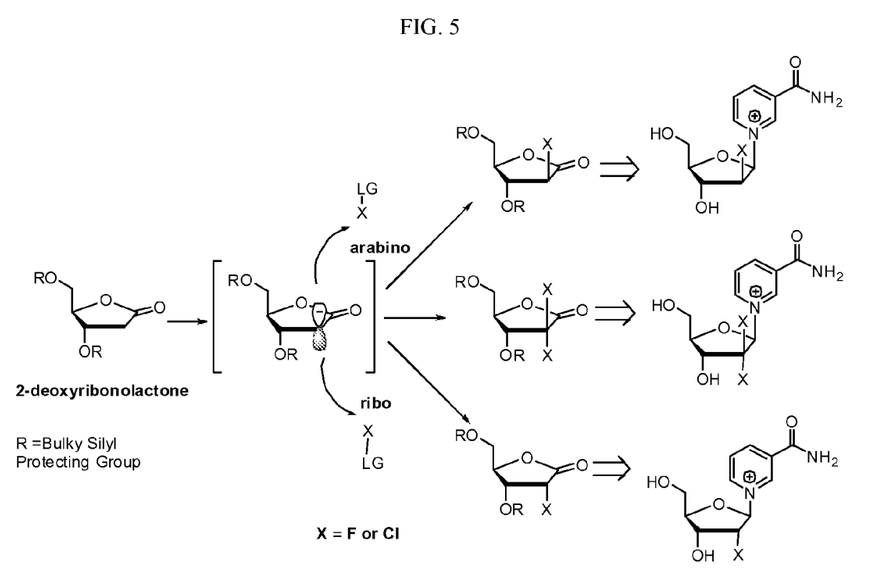
FIG. 5 illustrates a synthetic scheme to prepare compounds of formula (I) in accordance with an embodiment of the invention.

In particular embodiments, the compound is selected from the group consisting of nicotinamide riboside, nicotinic acid riboside, 1-(2'-deoxy-2',2'-difluoro-ribofuranosyl)-nicotinamide, 1-(2'-deoxy-2'-chloro-ribofuranosyl)-nicotinamide, methyl nicotinate riboside, ethyl nicotinate riboside, and a compound of the structure:

The compounds can be prepared as described in U.S. Patent Application Publication 2007/0117765 A1 and in U.S. Provisional Patent Application No. 61/222,424, filed Jul. 1, 2009, which is a priority document for International Patent Application No. PCT/US2010/040816. FIG. 5 illustrates an exemplary method for the synthesis of nicotinamide riboside analogs useful in accordance with particular embodiments of the invention.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "alkylene," as used herein, means a straight-chain or branched alkyl substituent containing from, for example, 1 to about 6 carbon atoms, preferably from 1 to about 4 carbon atoms, and is connected to two or more substituents at two or more different positions on the alkylene group.

The term "alkenyl," as used herein, means a linear alkenyl substituent containing at least one carbon-carbon double bond and from, for example, about 2 to about 6 carbon atoms (branched alkenyls are about 3 to about 6 carbons atoms), preferably from about 2 to about 5 carbon atoms (branched alkenyls are preferably from about 3 to about 5 carbon atoms), more preferably from about 3 to about 4 carbon atoms. Examples of such substituents include vinyl, propenyl, isopropenyl, n-butenyl, sec-butenyl, isobutenyl, tert-butenyl, pentenyl, isopentenyl, hexenyl, and the like.

The term "alkenylene," as used herein, means a straight-chain or branched alkenyl substituent containing from, for example, 2 to about 6 carbon atoms, preferably from 2 to about 4 carbon atoms, and is connected to two or more substituents at two or more different positions on the alkenylene group.

The term "alkynyl," as used herein, means a linear alkynyl substituent containing at least one carbon-carbon triple bond and from, for example, 2 to about 6 carbon atoms (branched alkynyls are about 3 to about 6 carbons atoms), preferably from 2 to about 5 carbon atoms (branched alkynyls are preferably from about 3 to about 5 carbon atoms), more preferably from about 3 to about 4 carbon atoms. Examples of such substituents include ethynyl, propynyl, isopropynyl, n-butynyl, sec-butynyl, isobutynyl, tert-butynyl, pentynyl, isopentynyl, hexynyl, and the like.

The term "alkynylene," as used herein, means a straight-chain or branched alkynyl substituent containing from, for example, 2 to about 6 carbon atoms, preferably from 2 to about 4 carbon atoms, and is connected to two or more substituents at two or more different positions on the alkynylene group.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The term "cycloalkenyl," as used herein, means the same as the term "cycloalkyl," however one or more double bonds are present. Examples of such substituents include cyclopentenyl and cyclohexenyl. The cyclic alkyl groups may be unsubstituted or further substituted with alkyl groups such as methyl groups, ethyl groups, and the like.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable bicyclic heterocyclyl groups include monocylic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. Preferably, the heterocyclyl group is an aromatic heterocyclyl group. Non-limiting examples of suitable heterocyclyl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, pyridinyl, pyrimidinyl, pyrazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heterocyclyl group is optionally substituted with 1, 2, 3, 4, or 5 substituents as recited herein, wherein the optional substituent can be present at any open position on the heterocyclyl group.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise $4n+2$ π electrons, according to Hückel's Rule.

The term "arylene" refers to an unsubstituted or substituted aromatic carbocyclic substituent as defined herein, wherein the arylene substituent is connected to two or more substituents at two or more different positions on the arylene group. For example, 1,2-dichlorobenzene can be considered to be a phenylene (arylene) group substituted with two chlorine atoms.

The term "arylalkyl," as used herein, refers to aryl group having an alkyl group attached thereto. The arylalkyl group can be substituted at any position of the aryl group or the alkyl group. The term "cycloalkylalkyl," as used herein, refers to cycloalkyl group having an alkyl group attached thereto. The cycloalkylalkyl group can be substituted at any position of the cycloalkyl group or the alkyl group.

Whenever a range of the number of atoms in a structure is indicated (e.g., a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (e.g., $C_6$-$C_{10}$) as used with respect to any chemical group (e.g., aryl) referenced herein encompasses and specifically describes 6, 7, 8, 9, and/or 10 carbon atoms, as appropriate, as well as any sub-range thereof (e.g., 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The invention also provides a method for treating a urea cycle disorder in a mammal, which method comprises administering to a mammal in need of treatment a therapeutically effective amount of a compound of the formula (I), wherein formula (I) is as described herein. In certain embodiments, the urea cycle disorder is selected from the group consisting of ornithine transcarbamoylase deficiency, carbamoyl phosphate synthetase deficiency, argininosuccinic aciduria, argininemia, hyperornithinemia, hyperammonemia, homocitrullinuria syndrome, lysinuric protein intolerance, citrullinemia, and N-acetylglutamate synthase deficiency. In preferred embodiments, the urea cycle disorder is hyperammonemia.

The compound can be administered in the form of a pharmaceutical composition comprising a pharmaceutically acceptable carrier and at least one compound described herein.

It is preferred that the pharmaceutically acceptable carrier be one that is chemically inert to the active compounds and one that has no detrimental side effects or toxicity under the conditions of use.

The choice of carrier will be determined in part by the particular compound chosen, as well as by the particular method used to administer the composition. Accordingly, there is a wide variety of suitable formulations of the pharmaceutical composition. The following formulations for oral, aerosol, nasal, pulmonary, parenteral, subcutaneous, intravenous, intra-arterial, intramuscular, intraperitoneal, intrathecal, intratumoral, topical, rectal, and vaginal administration are merely exemplary and are in no way limiting.

The pharmaceutical composition can be administered parenterally, e.g., intravenously, intraarterially, subcutaneously, intradermally, or intramuscularly. Thus, the invention provides compositions for parenteral administration that comprise a solution or suspension of the inventive compound dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In certain embodiments, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound may be made into suppositories by mixing with a variety of bases, such as emulsifying bases or water-soluble bases. Formulations suitable for vaginal administration may be presented as vaginal rings (i.e., intravaginal rings), pessaries, tampons, creams, gels, pastes, foams, or spray formulas containing, in addition to the active ingredient, such carriers as are known in the art to be appropriate.

It will be appreciated by one of ordinary skill in the art that, in addition to the afore described pharmaceutical compositions, the compound may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, for example hepatic cells, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9: 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound may be administered intravenously, locally, topically, etc. in a dose that varies according to the mode of administration, the agent being delivered, and the stage of disease being treated.

The invention additionally provides a compound of the formula (I):

wherein the compound is as described herein, for use in the treatment of a urea cycle disorder.

The invention further provides a method of assaying a sirtuin modulator, which method comprises (a) initiating a reaction of a sirtuin, a peptide substrate, and a radiolabelled NAD$^+$ in the presence or absence of a test compound to provide a reaction mixture, (b) loading the reaction mixture onto a purification column, (c) eluting the purification column with an eluent to provide fractions, (d) quantifying the radioactivity in the fractions, (e) determining a turnover rate from the radioactivity in the fractions, and (f) determining whether the test compound activated, inhibited, or had no effect on sirtuin activity.

In an embodiment, the sirtuin is SIRT5.

The following examples further illustrate the invention but, of course, should not be construed as in any way limiting its scope.

General Procedures

Synthetic peptides p300 (ERSTEL(K-Ac)TEI(K-Ac)EE-EDQPSTS) (SEQ ID NO: 1), H3 (ARTKQTAR(K-Ac)STGG(K-Ac)APRKQLA (SEQ ID NO: 2), H4 (SGGRG(K-Ac)GG(K-Ac)GLG(K-Ac)GGA(K-Ac)RHR) (SEQ ID NO: 3), JB12 (KKGQSTSRHK(K-Ac)LMFKTEG) (SEQ ID NO: 4), and cytochrome c (GDVEKGK(K-Ac)IFIMKCSQ) (SEQ ID NO: 5) were synthesized and characterized by the Proteomics Resource Center at Rockefeller University. Acetylated Bovine Serum Albumin (Promega, Madison, Wis.) was also used as a substrate. $NAD^+$ and all other reagents were purchased from Aldrich or VWR and were of the highest purity commercially available. A Hitachi Elite LaChrome system equipped with a diode array detector, $C_{18}$ reverse-phase columns and Beckman Coulter LS 6500 multipurpose scintillation counter was used for HPLC and radioactivity analyses.

EXAMPLE 1

This example demonstrates an assay for determination of the activation of SIRT5 in accordance with an embodiment of the invention.

Reactions containing $NAD^+$ including $[2,8_A{-}^3H]$-$NAD^+$, peptide substrate, with or without activator in 100 mM phosphate buffer (pH 7.5) were initiated by addition of SIRT5 enzyme to a concentration of 10 µM. Reactions were incubated at 37° C. for 1 h and quenched by addition of trifluoroacetic acid to pH 2. After centrifugation to remove the precipitates, reactions were loaded onto columns containing pre-equilibrated DEAE-Sephadex (equilibrated with 5 mM ammonium acetate pH 7). The reaction mixture was then eluted with eight fractions of 20 mM ammonium acetate pH 7 and three fractions of 300 mM ammonium acetate pH 7. The radioactivity contained in the eluents was then quantified by scintillation counter. Radiolabelled $NAD^+$ eluted in the 20 mM washes, while products ADPR and AADPR eluted in the 300 mM fractions. Radioactivity in the remaining $NAD^+$ fractions and the radioactivity in the product fractions were then converted to a turnover rate (1/s) by adjustment for specific radioactivity and enzyme concentration. The turnovers from the reaction with or without the activators were compared to show the percentage of activation.

EXAMPLE 2

This example demonstrates the effect of nicotinamide riboside and analogs on SIRT5 activity.

Test compounds were assayed against SIRT5 as described in Example 1. The results are set forth in the Table.

| Compound | SIRT5 |
|---|---|
| (pyridinium with B(OMe)$_2$ substituent, ribose 3'-phosphate) | 50% activated at 160 µM |
| (nicotinamide riboside with 2',2'-difluoro) | 90% activated at 2.4 mM |
| (nicotinic acid riboside) | 60% activated at 800 µM |
| (nicotinamide riboside) | 100% activated at 800 µM |
| (ethyl nicotinate riboside) | 40% activated at 600 µM |
| (methyl nicotinate riboside) | 80% activated at 600 µM |

TABLE-continued

| Compound | SIRT5 |
|---|---|
| (structure: nicotinamide riboside analog with OH, Cl on sugar) | 75% activated at 1 mM |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of increasing a deacetylase activity of SIRT5, wherein the method comprises contacting SIRT5 with an agent that binds SIRT5 and reduces the $K_m$ of SIRT5 for a substrate, thereby increasing the deacetylase activity of SIRT5, wherein the agent is a compound of the formula (I):

wherein $R^1$ and $R^2$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^3$ is hydrogen and $R^4$ is hydroxyl, $R^3$ and $R^4$ are fluoro, or $R^3$ is hydrogen and $R^4$ is chloro, $R^5$, $R^7$, $R^8$, and $R^9$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^7$ and $R^8$ taken together, or $R^8$ and $R^9$ taken together, form a 5- or 6-membered saturated or unsaturated ring, $R^6$ is $COR^{10}$ or $B(OR^{11})_2$, $R^{10}$ is selected from the group consisting of hydrogen, hydroxy, alkoxy, and aryloxy, and

$R^{11}$ is hydrogen or $C_1$-$C_6$ alkyl.

2. The method of claim 1, wherein $R^1$ is hydrogen or phosphate and $R^2$ is hydrogen.

3. The method of claim 1, wherein $R^6$ is $COR^{10}$ and $R^{10}$ is alkoxy or aryloxy.

4. The method of claim 1, wherein the SIRT5 is present in a eukaryotic cell.

5. A method for treating a urea cycle disorder in a mammal, which method comprises administering to a mammal in need of treatment a therapeutically effective amount of a compound of the formula (I):

wherein $R^1$ and $R^2$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^3$ is hydrogen and $R^4$ is hydroxyl, $R^3$ and $R^4$ are fluoro, or $R^3$ is hydrogen and $R^4$ is chloro, $R^5$, $R^7$, $R^8$, and $R^9$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^7$ and $R^8$ taken together, or $R^8$ and $R^9$ taken together, form a 5- or 6-membered saturated or unsaturated ring, $R^6$ is $COR^{10}$ or $B(OR^{11})_2$, $R^{10}$ is selected from the group consisting of hydrogen, hydroxy, alkoxy, and aryloxy, and $R^{11}$ is hydrogen or $C_1$-$C_6$ alkyl, thereby treating a urea cycle disorder in the mammal.

6. The method of claim 5, wherein $R^1$ is hydrogen or phosphate and $R^2$ is hydrogen.

7. The method of claim 5, wherein $R^6$ is $COR^{10}$ and $R^{10}$ is alkoxy or aryloxy.

8. The method of claim 5, wherein the urea cycle disorder is selected from the group consisting of ornithine transcarbamoylase deficiency, carbamoyl phosphate synthetase deficiency, argininosuccinic aciduria, argininemia, hyperornithinemia, hyperammonemia, homocitrullinuria syndrome, lysinuric protein intolerance, citrullinemia, and N-acetylglutamate synthase deficiency.

9. The method of claim 8, wherein the urea cycle disorder is hyperammonemia.

10. A method of increasing a deacetylase activity of SIRT5, wherein the method comprises contacting SIRT5 with an agent that binds SIRT5 and reduces the $K_m$ of SIRT5 for a substrate, thereby increasing the deacetylase activity of SIRT5, wherein the agent is a compound of the formula (I):

wherein $R^1$ and $R^2$ are independently selected from the group consisting of optionally substituted acyl, optionally substituted acyloxy, trialkylsilyl, optionally substituted alkyl, and optionally substituted alkylaryl, $R^3$ and $R^4$ are both fluoro, $R^5$, $R^7$, $R^8$, and $R^9$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^7$ and $R^8$ taken together, or $R^8$ and $R^9$ taken together, form a 5- or 6-membered saturated or unsaturated ring,

$R^6$ is $COR^{10}$, $R^{10}$ is amino, alkylamino, or dialkylamino, and $R^{11}$ is hydrogen or $C_1$-$C_6$ alkyl.

11. The method of claim 10, wherein the SIRT5 is present in a eukaryotic cell.

12. A method for treating a urea cycle disorder in a mammal, which method comprises administering to a mammal in need of treatment a therapeutically effective amount of a compound of the formula (I):

(I)

wherein $R^1$ and $R^2$ are independently selected from the group consisting of optionally substituted acyl, optionally substituted acyloxy, trialkylsilyl, optionally substituted alkyl, and optionally substituted alkylaryl, $R^3$ and $R^4$ are both fluoro, $R^5$, $R^7$, $R^8$, and $R^9$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^7$ and $R^8$ taken together, or $R^8$ and $R^9$ taken together, form a 5- or 6-membered saturated or unsaturated ring, $R^6$ is $COR^{10}$, $R^{10}$ is amino, alkylamino, or dialkylamino, and $R^{11}$ is hydrogen or $C_1$-$C_6$ alkyl, thereby treating a urea cycle disorder in the mammal.

13. The method of claim 12, wherein the urea cycle disorder is selected from the group consisting of ornithine transcarbamoylase deficiency, carbamoyl phosphate synthetase deficiency, argininosuccinic aciduria, argininemia, hyperornithinemia, hyperammonemia, homocitrullinuria syndrome, lysinuric protein intolerance, citrullinemia, and N-acetylglutamate synthase deficiency.

14. The method of claim 13, wherein the urea cycle disorder is hyperammonemia.

* * * * *

```
                        SEQUENCE LISTING

<160> NUMBER OF SEQ ID NOS: 5

<210> SEQ ID NO 1
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa is acetyllysine
<220> FEATURE:
<221> NAME/KEY: MISC_FEATURE
<222> LOCATION: (11)..(11)
<223> OTHER INFORMATION: Xaa is acetyllysine

<400> SEQUENCE: 1

Glu Arg Ser Thr Glu Leu Xaa Thr Glu Ile Xaa Glu Glu Glu Asp Gln
1               5                   10                  15

Pro Ser Thr Ser
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is acetyllysine
<220> FEATURE:
<221> NAME/KEY: MISC_FEATURE
<222> LOCATION: (14)..(14)
<223> OTHER INFORMATION: Xaa is acetyllysine
```

-continued

```
<400> SEQUENCE: 2

Ala Arg Thr Lys Gln Thr Ala Arg Xaa Ser Thr Gly Gly Xaa Ala Pro
1               5                   10                  15

Arg Lys Gln Leu Ala
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is acetyllysine
<220> FEATURE:
<221> NAME/KEY: MISC_FEATURE
<222> LOCATION: (9)..(9)
<223> OTHER INFORMATION: Xaa is acetyllysine
<220> FEATURE:
<221> NAME/KEY: MISC_FEATURE
<222> LOCATION: (13)..(13)
<223> OTHER INFORMATION: Xaa is acetyllysine
<220> FEATURE:
<221> NAME/KEY: MISC_FEATURE
<222> LOCATION: (17)..(17)
<223> OTHER INFORMATION: Xaa is acetyllysine

<400> SEQUENCE: 3

Ser Gly Gly Arg Gly Xaa Gly Gly Xaa Gly Leu Gly Xaa Gly Gly Ala
1               5                   10                  15

Xaa Arg His Arg
            20

<210> SEQ ID NO 4
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Xaa is acetyllysine

<400> SEQUENCE: 4

Lys Lys Gly Gln Ser Thr Ser Arg His Lys Xaa Leu Met Phe Lys Thr
1               5                   10                  15

Glu Gly

<210> SEQ ID NO 5
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is acetyllysine

<400> SEQUENCE: 5

Gly Asp Val Glu Lys Gly Lys Xaa Ile Phe Ile Met Lys Cys Ser Gln
1               5                   10                  15
```

UNITED STATES PATENT AND TRADEMARK OFFICE
CERTIFICATE OF CORRECTION

PATENT NO.         : 9,603,862 B2
APPLICATION NO.    : 13/516190
DATED              : March 28, 2017
INVENTOR(S)        : Anthony Sauve et al.

Page 1 of 1

It is certified that error appears in the above-identified patent and that said Letters Patent is hereby corrected as shown below:

In the Specification

Column 1, Line 16, under the heading "STATEMENT REGARDING FEDERALLY SPONSORED RESEARCH AND DEVELOPMENT" which reads:

"This invention was made with Government support under Grant Number R01 DK73466-05 awarded by the NIH. The Government has certain rights in this invention."

Should read:

"This invention was made with Government support under Grant Number DK073466 awarded by the National Institutes of Health. The Government has certain rights in this invention."

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*